United States Patent [19]

Satake et al.

[11] Patent Number: 4,884,434
[45] Date of Patent: Dec. 5, 1989

[54] WEAR SENSOR

[75] Inventors: Takeshi Satake, Itami, Japan; Yoshiyuki Imada, Fort Lee, N.J.

[73] Assignee: Mitsubishi Cable Industries, Ltd., Amagasaki, Japan

[21] Appl. No.: 309,988

[22] Filed: Feb. 13, 1989

Related U.S. Application Data

[63] Continuation of Ser. No. 89,761, Aug. 27, 1987, abandoned.

[30] Foreign Application Priority Data

Aug. 29, 1986 [JP] Japan ............................ 61-132838[U]

[51] Int. Cl.4 ..................... G01M 11/08; G01N 17/00; G08B 21/00
[52] U.S. Cl. ............................................ 73/7; 73/86; 250/227
[58] Field of Search ..................... 73/7, 86, 116, 118.1; 250/227; 340/52 A, 79

[56] References Cited

U.S. PATENT DOCUMENTS

| | | | |
|---|---|---|---|
| 3,958,445 | 5/1976 | Howard et al. | 73/7 |
| 4,143,319 | 3/1979 | Rouam | 73/7 |
| 4,184,145 | 1/1980 | Fima | 250/227 |
| 4,646,001 | 2/1987 | Balwin et al. | 340/52 A |
| 4,655,077 | 4/1987 | Purvis et al. | 73/86 |

FOREIGN PATENT DOCUMENTS

56-8524  1/1981  Japan ......................................... 73/7
62-163708 10/1987 Japan .

Primary Examiner—Tom Noland
Assistant Examiner—Robert P. Bell
Attorney, Agent, or Firm—Burns, Doane, Swecker & Mathis

[57] ABSTRACT

A wear sensor provided with a block incorporating one or more optical fibers for indicating that wear has occurred to the block, on the basis of a fact that the fibers have been severed on account of wear of the block.

10 Claims, 5 Drawing Sheets

WEAR SENSOR

This application is a continuation of application Ser. No. 089,761 filed Aug. 27, 1987 now abandoned.

BACKGROUND OF THE INVENTION

1. Field of the Invention

This invention relates to a wear sensor disposed to closely face the inner space of, for example, the cylinder incorporating a piston, and used for sensing wear of the inner wall or the like of the cylinder directly or indirectly.

2. Description of the Prior Art

The inner wall of a cylinder wears with reciprocal movement of a piston and conventional practice to find wear or the degree of wear has depended on visual observation after disassembling the cylinder when vibration arising from wear is sensorially recognized with the sense of hearing.

In short, when wear develops in an internal part of a unit, for example, the cyinder as described above, troublesome work is required for disassembling and thereafter, reassembling the unit. With respect to those units that are impossible to disassemble because of the use or the mechanism thereof, vibration caused by wear is observed by means of vibrograph, by which wear is indirectly observed. However, vibration is caused not only by wear but also by other factors. On the contrary, no vibration is caused sometimes even if wear develops. Therefore, such a method as indirect observation cannot reliable.

SUMMARY OF THE INVENTION

A first object of this invention is to provide a highly reliable wear sensor capable of exact sensing of wear.

A second object of this invention is to provide a wear sensor capable of inspecting wear without disassembling and re-assembling the object to be checked.

A third object of this invention is to provide a wear sensor free from the influence of vibration.

A fourth object of this invention is to provide a wear sensor capable of being constructed in small size.

A fifth object of this invention is to provide a wear sensor that permits a reduction in the number of peripheral component parts, that is, parts of the light source and related units.

For attaining these objects, a wear sensor according to this invention is provided with a block having optical waveguide members connected to the light source at one end and to the light receiving element at the other end.

The above and further objects and features of the invention will more fully be apparent from the following detailed description with accompanying drawings.

DETAILED DESCRIPTION OF THE INVENTION

Figure 1:
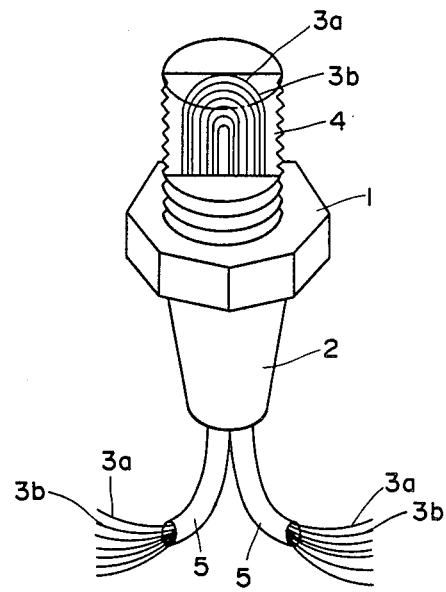
FIG. 1 is a partially broken perspective view of a wear sensor according to a first embodiment of this invention.
Figure 2:
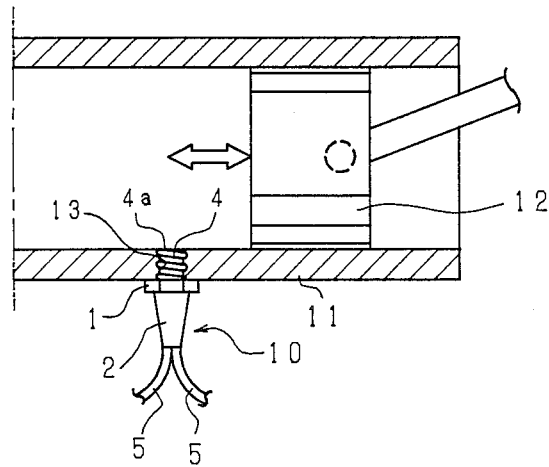
FIG. 2 is an illustrative view of a manner of using a wear sensor according to this invention.

FIG. 1 shows a wear sensor of this invention in a partially broken sectional view. A circular pillar-like block 4 is concentrically fixed to one surface of a flat polygonal pillar-like base 1 and a truncated conical protective cylinder 2 is fixed to the other surface with the diametrally large part thereof directed to the base 1. Optical fibers 3a, 3b, . . . connected to the light source (not shown) at one end and to the light receiving element (not shown) at the other end are buried as if molded in the block 4 so as to be located on the same plane including the axial center of the block 4. The optical fibers 3a, 3b, . . . are contained in sleeves 5 at other parts than buried in the block 4 and extend through the protective cylinder 2 toward the inner space of the block 4. In the block 4, the optical fibers 3a, 3b, . . . are bent to form semicircles on the side of the tip of the block and extend outward from the base surface. The center and the top of the curvature of each of optical fibers 3a, 3b, . . . are positioned on the axial center of the block 4. The optical fibers are arranged to form silimar figures in such pattern that the fiber 3a lying on the outermost side is bent at the largest radius and the immediate adjacent fiber 3b at the next-to-the-largest radius so that the tip surface of the block may be parallel with tangents to respective fibers at the extremity of curvature thereof. A distance between tops of curvatures of optical fibers 3a, 3b, . . . that is, a distance between optical fibers 3a and 3b at the axial center of the block is equal to those between the other fibers. Screw threads are formed on the periphery of the block 4. When making up a block, it is preferable to prepare beforehand a plurality of optical fibers bent and parallelly arranged to form a flat solidified collective body and bury this body in the block as if molding. Another method to clamp optical fibers with two semicircular pillarlike bodies may suffice for composing a block 4. A wear sensor 10 of the structure as above is, as shown in FIG. 2, screwed into a thread hole 13 on the wall of the cylinder 11 in such a manner that the tip of the sensor faces a zone through which the piston 12 passes. It is a matter of course that the tip surface of the wear sensor 10 must be flush with the inner surface of the cylinder 11.

With the repeated reciprocation of the piston 12 at high speed, the inner surface of the cylinder 11 gradually wears. Accordingly, the block 4 containing the wear sensor 10 also wears. As described above, the optical fibers 3a, 3b, . . are connected to the light source at one end and to the light receiving element at the other end. The light receiving element, therefore, receives light from the light source through optical fibers 3a, 3b, . . . and, with the development of wear of the wear sensor, that is, wear of the inner surface of the cylinder 11, the top of the curvature of the optical fiber 3a nearest the tip surface of the wear sensor wears while causing decrease in quantity of light to be received and, at last, wears out to breakage, when the quantity of light received by the light receiving element is reduced to zero.

Further development of wear causes the same phenomenon on the neighboring optical fiber 3b and a plurality of other fibers in turn. Accordingly, when distances between the tip surface of the block and the optical fiber 3a, between adjacent fibers 3a and 3b, and between other subsequent fibers as well as geometrical dimensions such as a diameter of the optical fiber are known beforehand, a degree of wear of the cylinder 11 can be found upon observation of the quantity and condition of the light received by the light receiving element.

Figure 3:
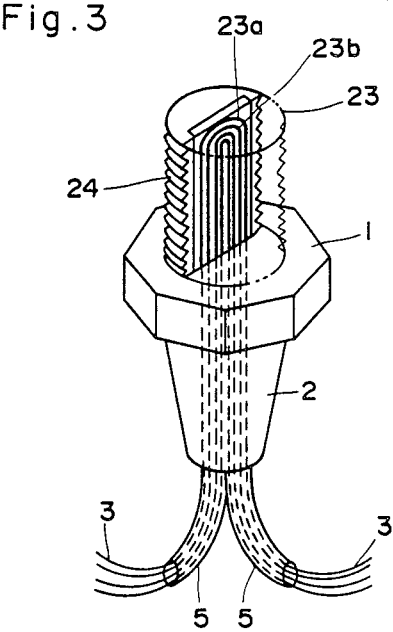
FIG. 3 is a partially broken perspective view of a wear sensor according to a second embodiment of this invention.
Figure 4:
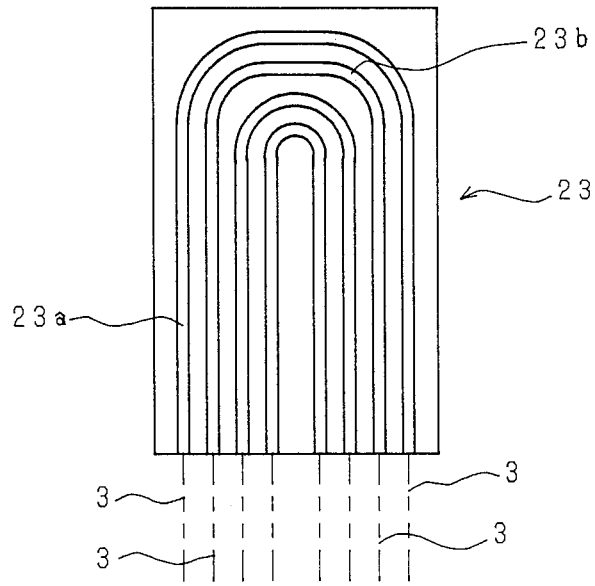
FIG. 4 is a view of a pattern of optical paths in the polymer optical waveguide of the second embodiment of this invention.

FIG. 3 shows the second embodiment of this invention. This embodiment is provided with a block 24 having a polymer optical waveguide 23 molded therein. The polymer optical waveguide 23 is in the form of a plate in which a plurality of optical paths 23a, 23b, . . . are formed of high molecules of high refractive index contained in those of low refractive index, curved to be semicircular at the side of the tip surface of the block 24, and extend toward the base side of the block in a manner similar to those in the first embodiment. FIG. 4 shows a pattern of this waveguide. Some of the optical paths 23a, 23b, . . . on the base side of the waveguide 23 are connected to optical fibers connected to the light source, whereas remaining ones are connected to optical fibers connected to the light receiving element. Rays of light incident to the optical paths 23a, 23b, . . . are transmitted to the ends of the paths without leaking outside thanks to differences between refractive indexes of molecules composing optical paths. In this embodiment, too, the block 24 wears together with the object of inspection such as a cylinder, and the optical paths 23a, 23b, . . . also wear one by one. Thus, the degree of wear can be measured by observing the quantity of light received by the light receiving element. In the second embodiment, as precision in forming a polymer optical waveguide 23 is higher than that in burying optical fibers as in the first embodiment, more accurate sensing of the degree of wear can be performed.

Figure 5:
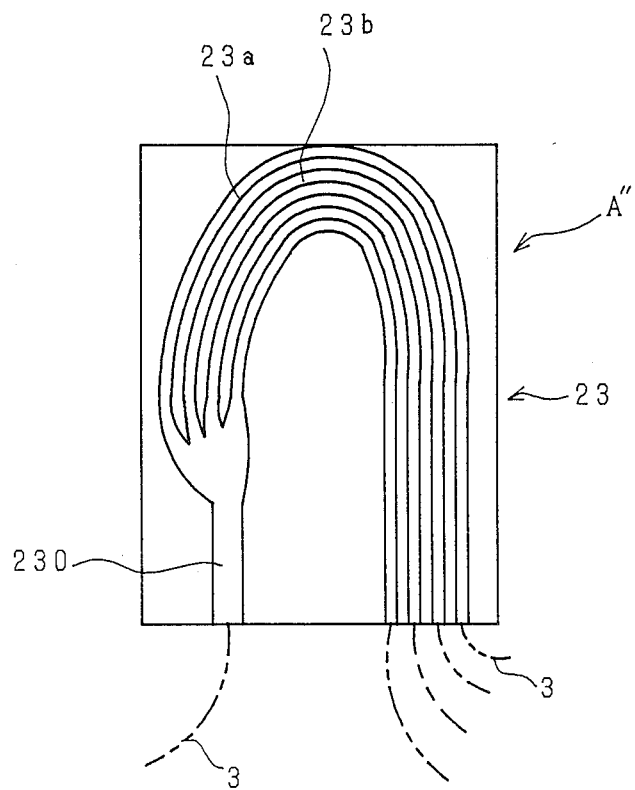
FIG. 5 is a view of a pattern of optical paths in the polymer optical waveguide of the third embodiment of this invention.
Figure 6:
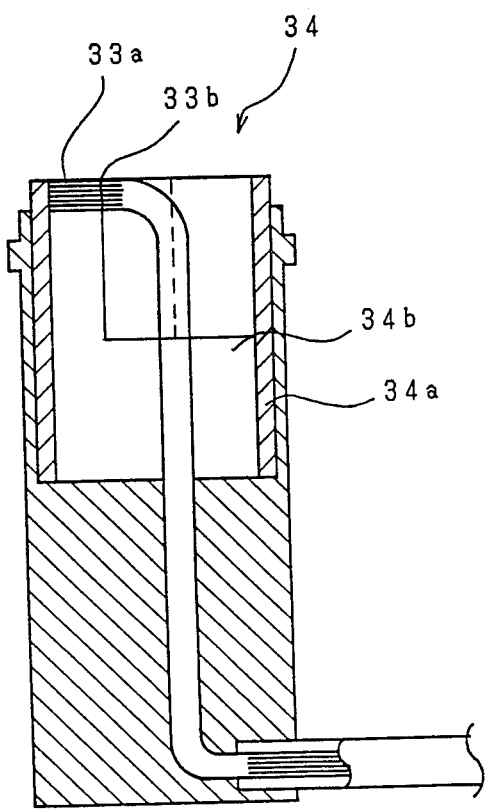
FIG. 6 is a sectional side view of the structure of the fourth embodiment of this invention wherein the block is a circular cylinder.
Figure 7:
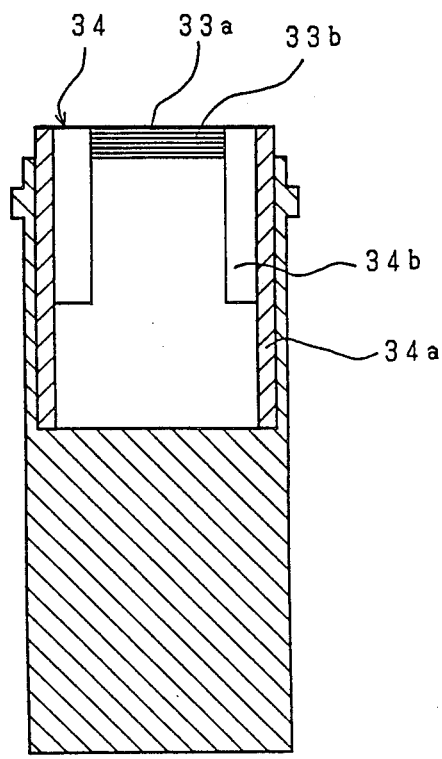
FIG. 7 is a sectional front view of the structure of FIG. 6.

FIG. 5 shows a pattern of optical paths in the third embodiment. The pattern of optical paths 23a, 23b, . . . of the polymer optical waveguide 23 is different from that in the second embodiment. That is to say, distances between optical paths 23a, 23b, . . . at the axial center of the block are the same as those in the second embodiment but the ends of paths on the side of the light source are consolidated into a single line of optical path 230. To the end of this path 230, an optical fiber 3 is connected, the optical fiber 3 being connected to the light source. The state on the side of the light receiving element is the same as in the second embodiment.

In this third embodiment, the number of parts on the side of the light source can advantageously be reduced to that required for a single line of system. FIGS. 6, 7, 8, and 9 are views of the fourth embodiment using optical fibers. A block 34 comprises a cylinder 34a, an inner block 34b disposed in the cylinder 34a, optical fibers 33a, 33b, . . . and resin 34c for filling up the inner space of the cylinder 34a. The inner block 34b has a curved surface extending along the inner surface of the cylinder 34a at a part of the periphery thereof, and a large number of optical fibers 33a, 33b, . . . are attached to the curved surface at fixed pitches near the tip surface of the block 34 and bent at a suitable position toward the base side of the block 34 so as to extend outward therefrom. A protective cylinder is disposed concentrically with and outside the block 34. The block 34 is made in such a way that optical fibers 33a, 33b, . . . are provided on the curved surface of the inner block 34b and, while the curved surface with optical fibers is pressed to the cylinder 34a, resin 34c is filled into the inner space of the cylinder 34a and hardened.

Figure 8:
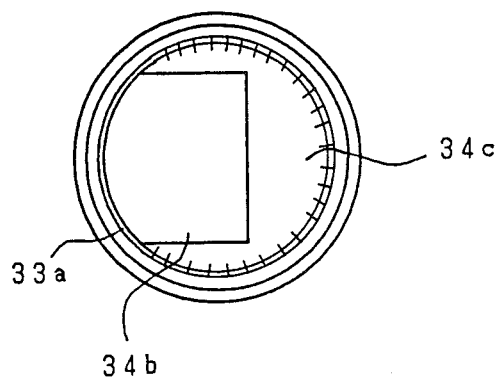
FIG. 8 is a plan view thereof.

In the embodiment shown in FIG. 1, since optical fibers are positioned on a plane passing through the center of the block, the optical fiber lying distant from the tip of the block (inner side) must be bent at a radius smaller than that for the optical fiber lying on the outer side, which results in a limit on the use of optical fibers. In contract to that embodiment, the optical fibers in the fourth embodiment arranged parallel to the center axis of the block and bent along the circumferential direction and thus, may be curved at the radius of the curved part of the inner block regardless of distances from the tip surface of the block. In other words, the radius of curvature of all of the fibers is substantially equal to the radius of curvature of the curved part of the inner block as shown in FIG. 8. As a result, the fibers can be positioned in a small-sized block in order to enable the manufacture of sensor of small size. Variation in the quantity of received light is similar to that in the above said embodiments and a description thereof is omitted.

Incidentally, a flat cable formed of a plurality of optical fibers arranged on a plane can be used as a group of optical fibers 33a, 33b, . . . in this fourth embodiment.

In the fourth embodiment, optical fibers are disposed within the cylinder 34a, however, they may be externally disposed on the periphery of the cylinder.

Figure 9:
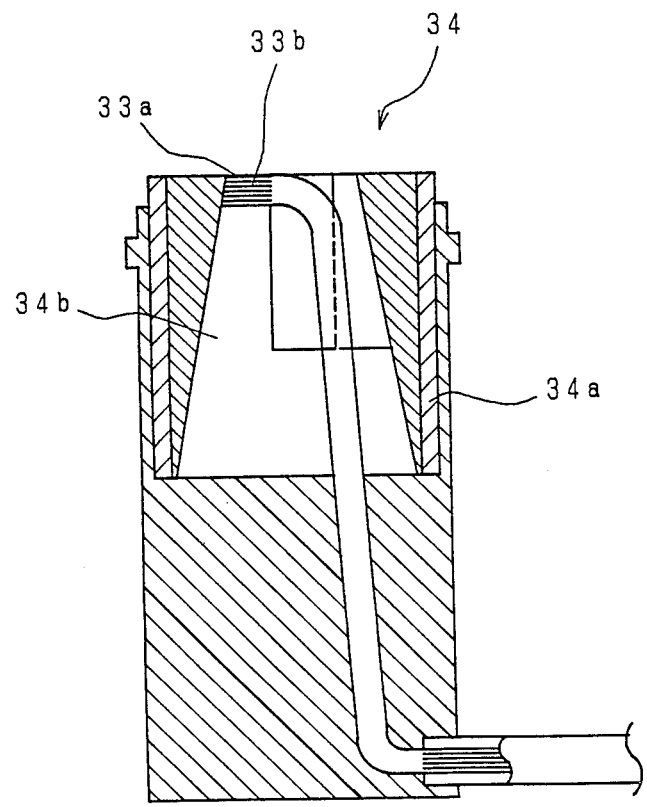
FIG. 9 is a sectional side view of the structure of the fourth embodiment of this invention wherein the block is a truncated cone.

The optical fibers 33a, 33b, . . . in the fourth embodiment are wound in the direction perpendicular to the generating line of a circular pillar, however, they may be wound in the direction perpendicular to the generating line of a truncated cone as shown in FIG. 9. In other words, an arrangement in which optical fibers are wound on a part of a surface of a truncated cone is possible. In the case of a structure as above, the number of optical fibers per unit length along the axial length of the truncated cone is large and, therefore, can provide a sensor having high power of wear sensing and analysis.

As described above, in any of the above said embodiments, wear is measured by means of rays of light and the quantity of light received is not varied by vibration. Accordingly, the degree of wear can be sensed irrespective of vibration.

The manner of utilizing this invention is not limited to an embodiment shown in FIG. 2 but is also applicable to sensing the wear on the side of piston. For example, when a piston 12 in a horizontal cylinder 11 is fitted with a piston ring and collars for keeping the posture of a piston, a wear sensor 10 of this invention is fixed to a lower internal surface of a part lying within a displacement area of the piston 12 but not within that of the piston ring or collar disposed in the outermost position on the piston side (for example, a position near the extremity of the stroke of the piston), so that the piston 12 may be in slide contact with the top surface of the wear sensor 10.

Since the piston ring or collar wears while sliding in the cylinder, the piston 12 descends and, in connection therewith, the wear sensor wears at the tip surface first and optical fibers or polymer optical waveguide wear to breakage.

A single line of optical fiber in the block may suffice according to the purpose of wear sensing.

A single line of optical path may suffice when the polymer optical waveguide is used.

Moreover, when a plurality of optical fibers or optical paths in the polymer optical waveguide are used, distances between fibers or optical paths in the direction along the development of wear may be either even or uneven. An important point is to specify such distances. This invention is also applicable to devices other than a combination of the piston and cylinder.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within the meets and bounds of the claims, or equivalence of such meets and bounds thereof are therefore intended to be embraced by the claims.

What is claimed is:

1. A wear sensor comprising:
    a block having a wearing surface, a periphery of said block including at least one curved surface; and
    a plurality of optical waveguide members, each having a segment disposed within said block substantially adjacent to and following the contour of said curved surface, said segments being successively disposed at spaced apart distances from one another in a direction parallel to a longitudinal axis of said block, a first and second end of each of said plurality of optical waveguide members being connected to a light source and a light receiving element, respectively, such that each member when intact transmits light from the light source to the light receiving element, said segments being arranged such that wear of said wearing surface causes successive breakage of individual segments.

2. A wear sensor as set forth in claim 1, wherein said optical waveguide members are optical fibers.

3. A wear sensor as set forth in claim 1, wherein said optical waveguide members serve as a polymer optical waveguide.

4. A wear sensor as set forth in claim 3, wherein said optical waveguide members are connected into a single optical path at one end of said polymer optical waveguide and into individual optical paths at the other end of said polymer optical waveguide.

5. A wear sensor as claimed in claim 1 wherein said block, is cylindrical.

6. A wear sensor as claimed in claim 5 wherein the optical waveguide members are integral with the periphery of said cylindrical block.

7. A wear sensor as claimed in claim 5 wherein the optical waveguide members are located underneath the periphery of said cylindrical block.

8. A wear sensor as claimed in claim 1 wherein said block is in the form of a truncated cone.

9. A wear sensor as claimed in claim 8 wherein the optical waveguide members are integral with the periphery of said truncated cone.

10. A wear sensor as claimed in claim 8 wherein the optical waveguide members are located underneath the periphery of said truncated cone.

* * * * *